(12) United States Patent
Nishizaki

(10) Patent No.: US 9,889,104 B2
(45) Date of Patent: Feb. 13, 2018

(54) AGENT FOR TREATING DIABETES

(71) Applicant: NISHIZAKI BIOINFORMATION RESEARCH INSTITUTE, Kobe-shi, Hyogo (JP)

(72) Inventor: Tomoyuki Nishizaki, Kobe (JP)

(73) Assignee: Nishizaki Bioinformation Research Institute, Kobe (JP)

( * ) Notice: Subject to any disclaimer, the term of this patent is extended or adjusted under 35 U.S.C. 154(b) by 0 days.

(21) Appl. No.: 15/110,286

(22) PCT Filed: Jan. 6, 2015

(86) PCT No.: PCT/JP2015/050122
§ 371 (c)(1),
(2) Date: Jul. 7, 2016

(87) PCT Pub. No.: WO2015/105094
PCT Pub. Date: Jul. 16, 2015

(65) Prior Publication Data
US 2016/0324815 A1    Nov. 10, 2016

(30) Foreign Application Priority Data
Jan. 7, 2014 (JP) ................. 2014-000905

(51) Int. Cl.
*A61K 31/20* (2006.01)
(52) U.S. Cl.
CPC .................. *A61K 31/20* (2013.01)
(58) Field of Classification Search
CPC .................................. A61K 31/20
See application file for complete search history.

(56) References Cited

U.S. PATENT DOCUMENTS

| 7,468,389 B2 | 12/2008 | Nishizaki et al. |
| 2005/0075393 A1 | 4/2005 | Nishizaki et al. |
| 2014/0315990 A1 | 10/2014 | Alkon et al. |
| 2015/0376213 A1 | 12/2015 | Nishizaki et al. |

FOREIGN PATENT DOCUMENTS

| JP | 2008-143819 A | 6/2008 |
| WO | WO 2002/050013 A1 | 6/2002 |
| WO | WO 2013/071282 A1 | 5/2013 |
| WO | WO 2014/126191 A1 | 8/2014 |

OTHER PUBLICATIONS

The New England Journal of Medicine, Feb. 7, 2002.*
Canetti et al., "Linoleic and alpha linolenic acids ameliorate streptozotocin-induced diabetes in mice," *Arch. Physiol. Biochem.*, 120(1): 34-39 (2014).
Schmitz-Peiffer et al., "Inhibition of PKCε Improves Glucose-Stimulated Insulin Secretion and Reduces Insulin Clearance," *Cell Metab.*, 6(4): 320-328 (2007).
European Patent Office, Extended European Search Report in European Patent Application No. 15735079.4 (dated Aug. 10, 2017).
Kanno et al., *Journal of Lipid Research*, 47(6): 1146-1156 (2006).
Kanno et al., *Journal of Neurochemistry*, 95(3): 695-702 (2005).
Nagata et al., *Psychogeriatrics*, 5: 122-126 (2005).
Tsuchiya et al., *The Journal of Physiological Sciences*, 64: S214, abstract 2P-155 (The 91st Annual Meeting of the PSJ, Mar. 16-18, 2014).
Yaguchi et al., *Neuroreport*, 17(1): 105-108 (2006).
Yamamoto et al., *Neuroscience*, 130(1): 207-213 (2005).
Japanese Patent Office, International Search Report in International Patent Application No. PCT/JP2015/050122 (dated Mar. 10, 2015).

* cited by examiner

*Primary Examiner* — Zohreh Fay
(74) *Attorney, Agent, or Firm* — Leydig, Voit & Mayer, Ltd.

(57) ABSTRACT

The present invention provides a prophylactic and/or therapeutic drug for diabetes, which contains 8-[2-(2-pentyl-cyclopropylmethyl)-cyclopropyl]-octanoic acid (DCP-LA) as an active ingredient, particularly a prophylactic and/or therapeutic drug for diabetes, which promotes sugar intake into the cells, and the like.

5 Claims, 2 Drawing Sheets

AGENT FOR TREATING DIABETES

CROSS-REFERENCE TO RELATED APPLICATIONS

This patent application is the U.S. national phase of International Patent Application No. PCT/JP2015/050122, filed on Jan. 6, 2015, which claims the benefit of Japanese Patent Application No. 2014-000905, filed Jan. 7, 2014, the disclosures of which are incorporated herein by reference in their entireties for all purposes.

TECHNICAL FIELD

The present invention relates to a novel use of 8-[2-(2-pentyl-cyclopropylmethyl)-cyclopropyl]-octanoic acid (DCP-LA), more particularly, use as a therapeutic drug for diabetes, which is based on an intracellular sugar uptake promoting action.

BACKGROUND ART

Diabetes is a disease in which the function of insulin becomes insufficient, the blood glucose level becomes high, and sugar is detected even in urine. Insulin is produced in and secreted from pancreatic β cells, promotes synthesis of glycogen (storage type glucose) from glucose in the liver and muscle, suppresses degradation of glycogen into glucose in the liver, and suppresses increase in the blood glucose level.

The number of patients is increasing mainly due to overeating, lack of exercise, obesity, stress, and genetic factors.

Diabetes is largely divided into type 1 diabetes showing absolute lack of insulin, and type 2 diabetes showing relative lack of insulin. Type 1 is basically treated with insulin injection, and type 2 is basically treated with diet and exercise therapy, though drug therapy is necessary when the blood glucose cannot be controlled well. For drug therapy, oral therapeutic drug for diabetes or insulin is used, both of which require improvement in terms of side effects, QOL and the like.

In addition, the condition developing lifestyle-related diseases such as hypertension, hyperlipidemia, diabetes and the like due to the accumulated visceral fat is referred to as metabolic syndrome, and has been widely recognized to increase the risk of developing arteriosclerotic diseases (myocardial infarction, cerebral infarction etc.). Accordingly, the prophylaxis or treatment of diabetes is necessarily effective for the prophylaxis or treatment of metabolic syndrome.

On the other hand, 8-[2-(2-pentyl-cyclopropylmethyl)-cyclopropyl]-octanoic acid (DCP-LA), which is a linoleic acid derivative, is a compound having a long-term enhancing action on synapse transmission efficiency, which can delay metabolism in the body and can maintain stable LTP (long-term potentiation)-like enhancement of synapse transmission (patent document 1).

Some reports have also been documented as regards DCP-LA. For example, it has been reported that DCP-LA activates PKC-ε selectively and directly (non-patent document 1), DCP-LA improves cognitive dysfunction of senescence accelerated mouse (non-patent document 2), DCP-LA increases release of γ aminobutyric acid from hippocampus nerve cells (non-patent document 3), DCP-LA improves cognitive dysfunction of amyloid β peptide or scopolamine-treated rat (non-patent document 4), and DCP-LA promotes hippocampal synaptic transmission with α7 nicotinic acetylcholine receptor expressed in glutamatergic presynaptic cell as a target (non-patent document 5). Furthermore, it has been reported in recent years that DCP-LA has an action to suppress nerve cell death induced by oxidative stress (patent document 2).

DOCUMENT LIST

Patent Documents patent document 1: WO 02/50013
patent document 2: JP-A-2008-143819

Non-Patent Document non-patent document 1: Kanno T et al., J Lipid Res., 2006, 47(6):1146-56.
non-patent document 2: Yaguchi T et al., Neuroreport, 2006, 23; 17(1):105-8.
non-patent document 3: Kanno T et al., J Neurochem., 2005, 95(3):695-702.
non-patent document 4: Nagata T et al., Psychogeriatrics, 2005, 5:122-126.
non-patent document 5: Yamamoto et al., Neuroscience 2005, 130(1):207-213.

SUMMARY OF THE INVENTION

Problems to be Solved by the Invention

The present invention aims to elucidate the pharmacological action of DCP-LA and an influence thereof on living organisms, and provide a novel use.

Means of Solving the Problems

The present inventor has surprisingly found, in the process of studying in depth the pharmacological action of DCP-LA and an influence thereof on living organisms, that DCP-LA has an action to promote intracellular sugar uptake, and such action enables effective function of DCP-LA as a prophylactic and/or therapeutic drug for diabetes, in addition to the pharmacological action useful for the improvement of cognitive function and conventionally known in DCP-LA, which resulted in the completion of the present invention. Accordingly, the present invention is as described below.

[1] A prophylactic and/or therapeutic drug for diabetes, comprising DCP-LA as an active ingredient.
[2] The drug of the above-mentioned [1], wherein diabetes is type 1 diabetes.
[3] The drug of the above-mentioned [1], wherein diabetes is type 2 diabetes.
[4] The drug of any of the above-mentioned [1]-[3], which promotes sugar uptake into the cells.
[5] An agent for promoting sugar uptake into the cells, comprising DCP-LA as an active ingredient.
[6] The agent of the above-mentioned [5], which is a reagent for study.
[7] A method for the prophylaxis and/or treatment of diabetes, comprising administering an effective amount of DCP-LA to a subject in need thereof.
[8] The method of the above-mentioned [7], wherein diabetes is type 1 diabetes.
[9] The method of the above-mentioned [7], wherein diabetes is type 2 diabetes.

[10] The method of any of the above-mentioned [7]-[9], which promotes sugar uptake into the cells.
[11] DCP-LA for use for the prophylaxis and/or treatment of diabetes.
[12] DCP-LA of the above-mentioned [11], wherein diabetes is type 1 diabetes.
[13] DCP-LA of the above-mentioned [11], wherein diabetes is type 2 diabetes.
[14] DCP-LA of any of the above-mentioned [11]-[13], which promotes sugar uptake into the cells.
[15] A method of promoting sugar uptake into the cells, comprising processing the cells with DCP-LA.

Effect of the Invention

DCP-LA has an action to promote sugar uptake into the cells, and a blood glucose level lowering action, and is useful as various reagents (agents) based on such actions, as well as a prophylactic and/or therapeutic drug for diabetes. Since the prophylactic and/or therapeutic drug of the present invention has action mechanism different from that of existing drugs, it can avoid side effects that pose problems on existing drugs. In addition, the agent of the present invention can be used as a reagent for study, which can be a useful tool for the development of such prophylactic or therapeutic drug.

DESCRIPTION OF EMBODIMENTS

Figure 1:
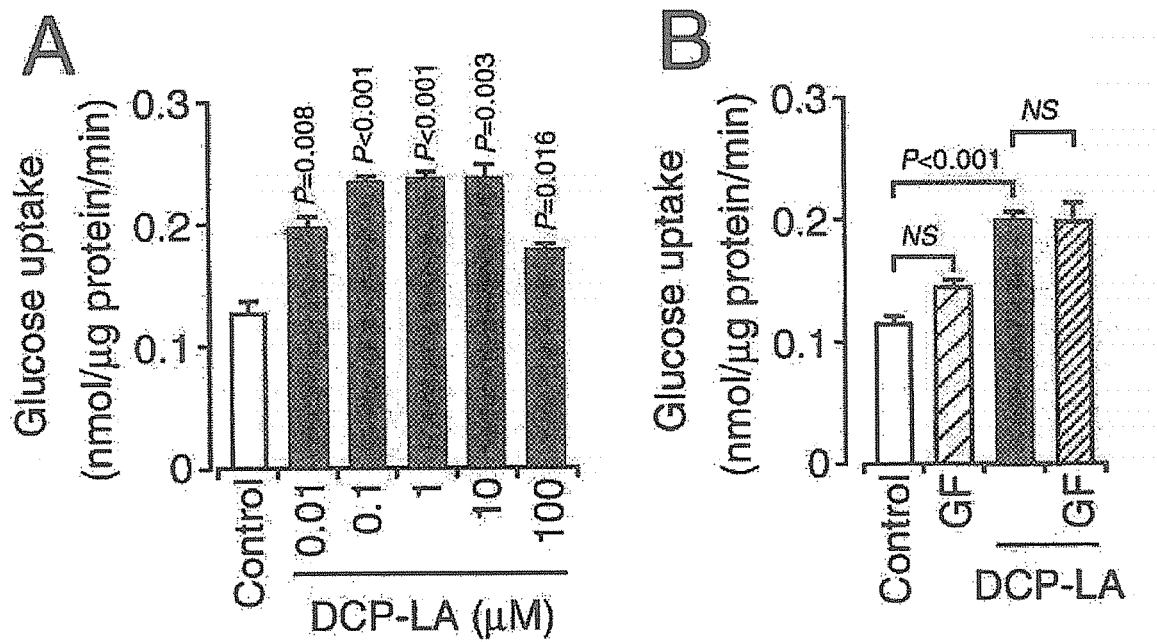
FIG. 1 is a graph showing the effect of DCP-LA on glucose uptake into 3T3L1-GLUT4myc adipocyte. (A) shows the measurement results of glucose concentration, obtained by incubating adipocytes in glucose-containing PBS in the presence or absence of DCP-LA, and then measuring the extracellular glucose level by HPLC. P value compared to control, Dunnett's test. (B) shows the measurement results of glucose concentration, obtained by incubating adipocytes in glucose-containing PBS in the presence or absence of DCP-LA and/or GF109203X(GF), and then measuring the extracellular glucose level by HPLC. In the graph, each column shows mean (±SEM) of glucose uptake (nmol/μg protein/min) (n=4 in each test). P value, Dunnett's test. NS, not significant.

The present invention is explained in detail in the following.

8-[2-(2-Pentyl-cyclopropylmethyl)-cyclopropyl]-octanoic acid (abbreviated as necessary as DCP-LA in the present specification) used in the present invention as an active ingredient has the following structural formula.

DCP-LA can be produced, for example, by the method shown in WO 02/50013. While DCP-LA has 4 optical isomers (α,α-DCP-LA, α,β-DCP-LA, β,α-DCP-LA, β,β-DCP-LA), all of such isomers and mixtures thereof are encompassed within the scope of the present invention. These isomers can be produced, for example, by the method shown in WO 2012/067111.

The DCP-LA in the present invention may also be used in the form of a salt thereof. Such salt is not particularly limited, and a salt acceptable as a medicine or food is preferable. Examples thereof include salts with inorganic base (e.g., alkali metal such as sodium, potassium and the like; alkaline earth metal such as calcium, magnesium and the like; aluminum, ammonium), organic base (e.g., trimethylamine, triethylamine, pyridine, picoline, ethanolamine, diethanolamine, triethanolamine, dicyclohexylamine, N,N-dibenzylethylenediamine), inorganic acid (e.g., hydrochloric acid, hydrobromic acid, nitric acid, sulfuric acid, phosphoric acid), organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acid (e.g., arginine, lysine, ornithine) or acidic amino acid (e.g., aspartic acid, glutamic acid) and the like.

When used in the present specification, the test subject can be a mammal. Examples of such mammal include primates (e.g., human, monkey, chimpanzee), rodents (e.g., mouse, rat, guinea pig), pets (e.g., dog, cat, rabbit), working animals and domestic animals (e.g., bovine, horse, swine, sheep, goat), with preference given to human.

DCP-LA has, as shown in the Examples with data, (1) an action to promote sugar uptake into the cells, and (2) an action to lower the blood glucose level of diabetes model mouse.

(1) Action to Promote Sugar Uptake into the Cells

Intracellular glucose uptake is performed via GLUT4 (glucose transporter 4) expressed on the cellular membrane surface of adipocyte and skeletal muscle cell. Intracellular uptake of glucose lowers the blood glucose level. DCP-LA can lower the blood glucose level by promoting the intracellular uptake of glucose.

As used herein, the "cell" is not particularly limited as long as it is capable of glucose uptake, and adipocyte, skeletal muscle cell, hepatocyte and the like can be mentioned.

(2) Blood Glucose Level-Lowering Action

Since DCP-LA can lower the blood glucose level without using insulin, it is useful for the treatment of type 2 diabetes.

By these superior pharmacological actions, the present invention is useful as a prophylactic and/or therapeutic drug for diabetes, as well as a prophylactic and/or therapeutic drug for metabolic syndrome (hereinafter to be also referred to as the medicine of the present invention). As used in the present specification, "prophylaxis" means prevention of exteriorization of symptoms in test subjects free from such symptoms, and the "treatment" means mitigation of symptoms, prevention or delay of exacerbation of symptoms in test subjects showing such symptoms.

In addition, by such pharmacological action of DCP-LA, the present invention can provide a method of promoting sugar uptake into the cells, a method for the prophylaxis and/or treatment of diabetes (type 1 diabetes, type 2 diabetes), and a method for the prophylaxis and/or treatment of metabolic syndrome (hereinafter to be also simply referred to as the method of the present invention).

When used in the present specification, the cell to be the target of processing with DCP-LA is not particularly limited as long as it can express GLUT4 and uptake glucose, and adipocyte, skeletal muscle cell, hepatocyte and the like can be mentioned. These cells may be induced to differentiate from progenitor cells by a method known per se. For example, adipocyte may be induced to differentiate from 3T3L1 fibroblast.

As used herein, the "processing" means contacting the above-mentioned cell with DCP-LA for a time necessary and sufficient. While the time varies depending on the desired effect and the kind of the cells to be used, it is generally 0.1-6 hr, preferably about 0.5-2 hr. Conveniently, it is performed by cultivation in a culture medium containing DCP-LA.

The medicine of the present invention varies depending on the age and condition of individual patients to be treated. In the case of intravenous administration, the daily dose of DCP-LA is 0.001-100 mg per 1 kg body weight of human or animal; in the case of intramuscular administration, the daily dose of DCP-LA is 0.001-10 mg per 1 kg body weight of human or animal; and in the case of oral administration, the daily dose of DCP-LA is 0.01-100 mg per 1 kg body weight of human or animal, which are generally given for the prophylaxis and/or treatment of diabetes, or for the prophylaxis and/or treatment of metabolic syndrome.

The medicine of the present invention can contain, besides DCP-LA which is the active ingredient, any additive, for example, a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatic substances such as citric acid, menthol, glycyllysin-ammonium salt, glycine, orange powder and the like, preservatives such as sodium benzoate, sodium bisulfite, methylparaben, propylparaben and the like, stabilizers such as citric acid, sodium citrate, acetic acid and the like, suspending agents such as methylcellulose, polyvinylpyrrolidone, aluminum stearate and the like, dispersing agents such as surfactant and the like, diluents such as water, saline, orange juice and the like, base waxes such as cacao butter, polyethylene glycol, kerosene and the like, and the like.

In one embodiment, the medicine of the present invention can be formulated as a preparation preferable for oral administration. Examples of the preparation preferable for oral administration include a liquid wherein an effective amount of a substance is dissolved in a diluent such as water and saline, a capsule, granule, powder or tablet containing an effective amount of a substance as a solid or granules, a suspension wherein an effective amount of a substance is suspended in a suitable dispersion medium, an emulsion wherein a solution of an effective amount of a substance is dispersed and emulsified in a suitable dispersion medium, and the like.

In another embodiment, the medicine of the present invention can be formulated as a preparation preferable for parenteral administration. Examples of the preparation preferable for parenteral administration (e.g., intravenous injection, subcutaneous injection, muscular injection, topical injection and the like) include aqueous and nonaqueous isotonic aseptic injection liquids, which may contain antioxidant, buffer, bacteriostatic, isotonicity agent and the like. In addition, examples thereof include aqueous and nonaqueous aseptic suspensions, which may contain suspension, solubilizer, thickener, stabilizer, preservative and the like. Unit dose or plural doses of the preparation can be filled in a container such as ampoule and vial. Moreover, the active ingredient and a pharmaceutically acceptable carrier can be freeze-dried and preserved in a form that can be dissolved or suspended in a suitable aseptic vehicle immediately before use.

DCP-LA can be provided as food. DCP-LA as an active ingredient has, as mentioned above, (1) an action to promote sugar uptake into the cells, and (2) an action to lower the blood glucose level in mammals (e.g., mouse, rat, hamster, rabbit, cat, dog, bovine, sheep, monkey, human and the like), and can be provided as a functional food effective for the prophylaxis or treatment of diabetes or for the prophylaxis or treatment of metabolic syndrome.

The "food" in the present invention means all foods and drinks other than pharmaceutical products and quasi-drugs. For example, it includes, but is not limited to, food for specified health uses, food with nutrient function claims, and what is called supplements.

The medicine or food of the present invention may be packed or filled individually by a unit ingestion amount or a divided amount of the medicine or food, or packed or filled comprehensively by many unit ingestion amounts or divided amounts thereof.

When the medicine or food of the present invention is provided as a single preparation or food, the unit ingestion amount of the medicine or food or a divided amount thereof is the unit ingestion amount of DCP-LA or a divided amount thereof.

Examples of the medicine or food wherein a unit ingestion amount or a divided amount thereof is packed or filled individually include general packages (e.g., PTP (press through packing) sheet, paper container, film (e.g., plastic film) container, glass container, plastic container) packed or filled with the unit ingestion amount or a divided amount thereof. The medicine or foods that are individually packed or filled may be further combined and packed or filled in a single container (e.g., paper container, film (e.g., plastic film) container, glass container, plastic container). Examples of the medicine or food wherein many unit ingestion amounts or a divided amount thereof are/is comprehensively packed or filled include those wherein many tablets or capsules are packed or filled in a single container (e.g., paper container, film (e.g., plastic film) container, glass container, plastic container) without distinction. The medicine or food of the present invention may contain a unit ingestion amount or a divided amount thereof in a number sufficient for long-term ingestion. For example, a food can contain same in a number sufficient for ingestion for not less than 3 days, preferably not less than 7 days, 10 days, 14 days or 21 days, or 1 month, 2 months, or not less than 3 months.

Furthermore, DCP-LA has, as mentioned above, (1) an action to promote sugar uptake into the cells, and (2) an action to lower the blood glucose level, and can also be provided as various reagents. As the reagent, a promoter of sugar uptake into the cells can be specifically mentioned. The reagent can be a useful tool for the development of a prophylactic and/or therapeutic drug for diabetes and metabolic syndrome, which has a new action mechanism conventionally not present, has reduced side effects, and/or has more enhanced effect.

The contents disclosed in any publication cited in the present specification, including patents and patent applications, are hereby incorporated in their entireties by reference, to the extent that they have been disclosed herein.

While the present invention is explained in further detail in the following by referring to Examples, it is not limited by the following Examples and the like.

EXAMPLES

Example 1

Verification of Action to Promote Sugar Uptake into the Cells (Material and Method)
1. Cell culture 3T3L1-GLUT4myc fibroblast strain expressing GLUT4myc was used. The cells are constructed by inserting human c-MYC epitope (14 amino acids) into the first ectodomain. It is possible to track transport of GLUT4 onto cell membrane surface by using an antic-myc antibody.

The cells were cultured in Dulbecco's Modified Eagles Medium (DMEM) added with 10% (v/v) bovine serum, penicillin (final concentration, 100 U/ml) and streptomycin (final concentration, 0.1 mg/ml) in a humid environment under 5% $CO_2$ and 95% air at 37° C. When the cells reached confluence (day 0), the medium was exchanged with DMEM added with 10% (v/v) fetal bovine serum (FBS), 1 μM dexamethasone, 0.5 mM 3-isobutyl-methyl-xanthine and 0.1 mg/ml insulin to allow for differentiation from fibroblast into adipocyte. The medium was exchanged with DMEM added with 10% (v/v) FBS on day 3, day 7 and day 11. On day 14, the cell differentiated into adipocyte were used for the experiment.

2. Glucose Uptake Assay

3T3L1-GLUT4myc adipocytes were incubated in Krebs-Ringer-HEPES buffer [136 mM NaCl, 4.7 mM KCl, 1.25 mM $CaCl_2$, 1.25 mM $MgSO_4$ and 20 mM HEPES, pH 7.5] containing 0.2% (w/v) bovine serum albumin (BSA) and added with 10 mM glucose at 37° C. for 1 hr. The cells were processed with DCP-LA and/or GF109203X in phosphate buffered saline (PBS) containing 10 mM glucose at 37° C. for 2 hr. After the processing, an extracellular solution was recovered and glucose was labeled with paraaminobenzoic acid ethylester (ABEE). Then, the ABEE-labeled solution (5 μl) was injected into the column (150×4.6 mm) of a high performance liquid chromatography (HPLC) system. ABEE-labeled glucose was detected using a fluorescence detector at an excitation wavelength 305 nm and a fluorescence wavelength 360 nm. The amount of glucose uptaken into the cells after incubation for 2 hr is calculated by subtracting the extracellular glucose concentration from the initial extracellular glucose concentration (10 mM).

3. GLUT4 Mobilization Monitoring

3T3L1-GLUT4myc adipocytes were incubated in Krebs-Ringer-HEPES buffer containing 0.2% (w/v) BSA and added with 10 mM glucose at 37° C. for 1 hr. The cells were processed with DCP-LA for 20 min. Then, the cells were homogenized by sonication in an ice-cooled mitochondria buffer [210 mM mannitol, 70 mM sucrose, and 1 mM ethylenediaminetetraacetic acid (EDTA), 10 mM HEPES, pH 7.5] containing 1% (v/v) protease inhibitor cocktail. Sequentially, the homogenate was centrifuged at 4° C. for 5 min at 3,000 rpm. The supernatant was further centrifuged at 4° C. for 15 min at 11,000 rpm. The recovered supernatant was ultracentrifuged at 4° C. for 60 min at 100,000 g, and separated into a cytoplasm fraction and a cellular membrane fraction. The supernatant was used as the cytoplasm fraction and the pellet was used as the cellular membrane fraction. Whether the cytoplasm component and the cellular membrane component could be successfully separated was confirmed by Western blot analysis using an antibody to lactate dehydrogenase (LDH) which is a cytoplasm component marker, and an antibody to cadherin which is a cellular membrane marker.

The protein concentration of each fraction was measured using BCA protein assay kit (Thermo Fisher Scientific, Waltham, Mass., USA). The protein of the cellular membrane fraction was resuspended in a mitochondria buffer containing 1% (w/v) sodium dodecyl sulfate (SDS). The protein of each fraction was separated by SDS-polyacrylamide gel electrophoresis (SDS-PAGE), and transferred onto polyvinylidene difluoride membranes. The blotting membranes were blocked with TBS-T [150 mM NaCl, 0.1% (v/v) Tween20 and 20 mM Tris, pH 7.5] containing 5% (w/v) BSA, reacted with anti-c-myc antibody (Merck Millipore, Darmstadt, Germany), and thereafter reacted with horseradish peroxidase (HRP) conjugate goat anti-mouse IgG antibody. The immunoreactivity was detected using ECL kit (Invitrogen), and visualized using a chemical luminescence detection system (chemiluminescence detection system; GE Healthcare, Piscataway, N.J., USA). The signal density was measured using an image analysis software (Image Gauge software; GE Healthcare).

(Results)

3T3L1-GLUT4myc adipocytes were incubated in glucose-containing (10 mM) PBS in the presence or absence of a given concentration of DCP-LA for 2 hr, and extracellular glucose concentration was measured by HPLC. The amount of glucose (nmol/μg protein/min) uptaken into the cells was calculated from the difference in the extracellular glucose concentration before and after incubation. The results are shown in FIG. 1A.

Separately, moreover, 3T3L1-GLUT4myc adipocytes were incubated in glucose-containing (10 mM) PBS for 2 hr in the presence or absence of 0.1 μM DCP-LA, and/or in the presence or absence of 0.1 μM GF109203X (GF), and then extracellular glucose concentration was measured by HPLC. The amount of glucose (nmol/μg protein/min) uptaken into the cells was calculated from the difference in the extracellular glucose concentration between before and after incubation. The results are shown in FIG. 1B.

The results of FIG. 1A show that DCP-LA has an action to promote sugar uptake into the adipocytes in a bell-shaped concentration-dependent manner. Since the results of FIG. 1B show that the sugar uptake promoting action of DCP-LA was not inhibited even in the presence of a PKCε inhibitor GF109203X, it was clarified that the sugar uptake promoting action of DCP-LA is irrelevant to the PKCε activation action of DCP-LA.

Then, 3T3L1-GLUT4myc adipocyte processed with 100 nM DCP-LA for 20 min and unprocessed 3T3L1-GLUT4myc adipocyte (control) were dissolved to prepare cytoplasm fraction (C) and cellular membrane fraction (M). The degree of transport of GLUT4 onto the cellular membrane surface was examined using an anti-c-myc antibody. The results are shown in FIG. 2.

Figure 2:
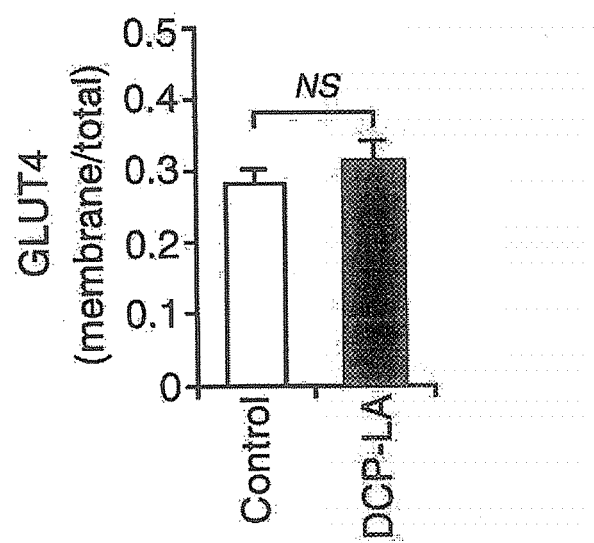
FIG. 2 shows that the intracellular sugar uptake promoting action of DCP-LA is not one caused by the stimulation of transport of GLUT4 to cellular membrane. 3T3L1-GLUT4myc adipocyte processed with DCP-LA, or unprocessed 3T3L1-GLUT4myc adipocyte (Control) was dissolved and separated into cytoplasm fraction (C) and cellular membrane fraction (M). Each fraction was subjected to Western blotting using anti-c-myc antibody. In the graph, each column shows mean (±SEM) of the ratio of (c-myc signal intensity in cellular membrane fraction)/(c-myc signal intensity in total cell) (n=4 in each test). NS, not significant; unpaired t-test

The results of FIG. 2 show that the transport of GLUT4 onto the cellular membrane was not promoted significantly by the processing with DCP-LA. Therefore, it was clarified that the intracellular sugar uptake promoting action of DCP-LA is not caused by stimulation resulting from the transport of GLUT4 onto a cellular membrane.

Example 2

Verification of Blood Glucose Level Lowering Action of DCP-LA (Material and Method)
Glucose Tolerance Test Type 1 diabetes model mouse was prepared by intraperitoneal administration of streptozotocin (STZ; 250 mg/kg) to C57BL/6J mouse (8-week-old) (Japan SLC Inc.; Shizuoka, Japan). After 4 days from the STZ administration, an oral glucose tolerance test (OGTT) was performed.

As type 2 diabetes model mouse, C57BL/KsJ-lepr$^{db}$/lepr$^{db}$ mouse (female, 8-week-old) (CLEA Japan; Tokyo, Japan) was used.

OGTT was performed using the mouse starved for 12 hr. Glucose (2 g/ml/kg body weight) was administered by gavage, and the time point thereof was taken as 0 h. DCP-LA (0, 0.001, 0.01, 0.1 mg/kg) was orally administered 30 min before administration of glucose. The blood (10 μl) was collected from the tail vein at the time points of 0, 30, 60, and 90 min, and each plasma sample which was labeled with ABEE and prepared from the obtained blood was loaded on high performance liquid chromatography (HPLC) system (LC-10ATvp; Shimadzu Co., Kyoto, Japan). The glucose concentration was calculated from a peak area/concentration analytical curve prepared using the standard glucose solution.

(Results)

Figure 3:
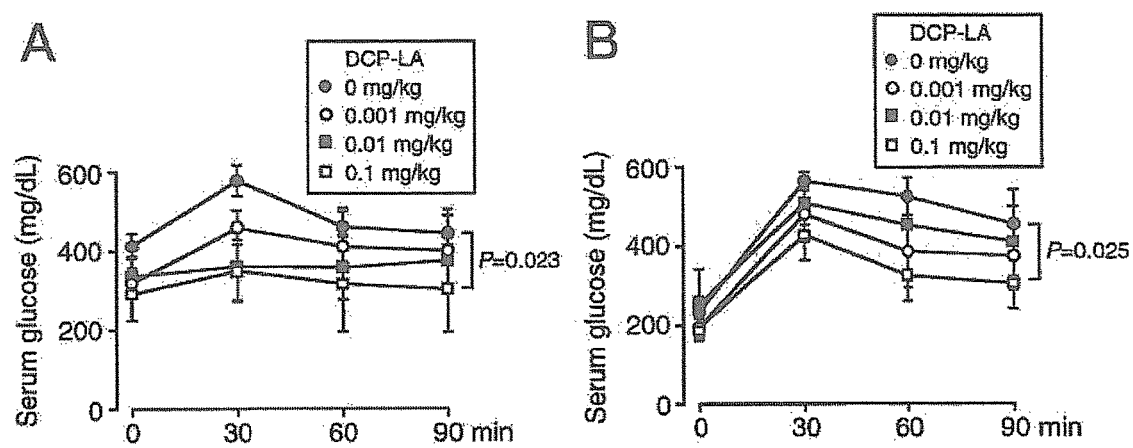
FIG. 3 shows the advantageous effect of DCP-LA on type 1 diabetes (DM) model mouse (A) and type 2 DM model mouse (B). As the type 1 DM mouse, C57BL/6J mouse processed with streptozocin (STZ) was used, and C57BL/KsJ-lepr$^{db}$/lepr$^{db}$ mouse was used as the type 2 DM model mouse. After glucose starvation for 12 hr, glucose (2 g/kg) was orally administered to each mouse and the blood glucose level was measured over time. In the graph, each point shows mean (±SEM) of blood glucose level (n=4-8 in each test). P value, Fisher's PLSD (protected least significant difference) method

The results obtained using type 1 diabetes model mouse are shown in FIG. 3A, and the results obtained using type 2 diabetes model mouse are shown in FIG. 3B. These results show that DCP-LA has an action to dose-dependently lower the blood glucose level in type 1, type 2 diabetes model mice. Therefore, the present invention suggests the possibility of providing a therapeutic drug for type 1 diabetes and type 2 diabetes.

INDUSTRIAL APPLICABILITY

DCP-LA has an action to promote sugar uptake into the cells, and a blood glucose level lowering action, and is useful as various reagents (agents) based on such actions, as well as a prophylactic and/or therapeutic drug for diabetes. Since the prophylactic and/or therapeutic drug of the present invention has action mechanism different from that of existing drugs, it can avoid side effects that pose problems on existing drugs. In addition, the agent of the present invention can be used as a reagent for study, which can be a useful tool for the development of such prophylactic or therapeutic drug.

This application is based on a patent application No. 2014-000905 filed in Japan (filing date: Jan. 7, 2014), the contents of which are incorporated in full herein.

The invention claimed is:

1. A method of treating diabetes, comprising administering an effective amount of 8-[2-(2-pentyl-cyclopropylmethyl)-cyclopropyl]-octanoic acid to a subject in need thereof.

2. The method according to claim 1, which promotes sugar uptake into cells.

3. A method of promoting sugar uptake into cells, comprising processing the cells with 8-[2-(2-pentyl-cyclopropylmethyl)-cyclopropyl]-octanoic acid.

4. The method according to claim 1, wherein the diabetes is type 1 diabetes.

5. The method according to claim 1, wherein the diabetes is type 2 diabetes.

* * * * *